(12) United States Patent
Eckermann et al.

(10) Patent No.: US 9,284,347 B2
(45) Date of Patent: Mar. 15, 2016

(54) CHROMATOGRAPHIC METHOD FOR PURIFYING FC-CONTAINING PROTEINS

(75) Inventors: Christian Eckermann, Biberach an der Riss (DE); Dorothee Ambrosius, Laupheim (DE); Franz Nothelfer, Biberach an der Riss (DE); Thomas Rathjen, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 554 days.

(21) Appl. No.: 13/522,030

(22) PCT Filed: Jan. 21, 2011

(86) PCT No.: PCT/EP2011/050817
§ 371 (c)(1),
(2), (4) Date: Nov. 9, 2012

(87) PCT Pub. No.: WO2011/089212
PCT Pub. Date: Jul. 28, 2011

(65) Prior Publication Data
US 2013/0197197 A1   Aug. 1, 2013

(30) Foreign Application Priority Data
Jan. 22, 2010  (EP) .................................. 10151416
Aug. 5, 2010  (EP) .................................. 10171975

(51) Int. Cl.
C07K 1/00    (2006.01)
C07K 1/22    (2006.01)
A61K 39/395  (2006.01)
C07K 16/00   (2006.01)

(52) U.S. Cl.
CPC ............. *C07K 1/22* (2013.01); *A61K 39/39591* (2013.01); *C07K 16/00* (2013.01); *C07K 2317/14* (2013.01)

(58) Field of Classification Search
None
See application file for complete search history.

(56) References Cited

U.S. PATENT DOCUMENTS

| | | | |
|---|---|---|---|
| 5,874,218 A * | 2/1999 | Drolet .............. | A61K 47/48076 435/6.11 |
| 5,932,428 A * | 8/1999 | Dubrow et al. .............. | 435/7.24 |
| 2005/0176109 A1 | 8/2005 | Yumioka et al. | |
| 2007/0172846 A1* | 7/2007 | Zhang et al. ...................... | 435/6 |
| 2008/0064860 A1* | 3/2008 | Sun et al. ...................... | 530/413 |
| 2012/0141497 A1* | 6/2012 | Gallo et al. ................ | 424/158.1 |
| 2012/0283416 A1* | 11/2012 | Frauenschuh et al. ..... | 530/387.3 |

FOREIGN PATENT DOCUMENTS

| | | |
|---|---|---|
| WO | 2007109163 A2 | 9/2007 |
| WO | 2008031020 A2 | 3/2008 |
| WO | 2011073389 A1 | 6/2011 |

OTHER PUBLICATIONS

International Search Report, Form PCT/ISA/210, and Written Opinion, Form PCT/ISA/237, for corresponding PCT/EP2011/050817; date of mailing: Mar. 3, 2011.
Arakawa T. et al, Elution of antibodies from a Protein-A column by aqueous arginine solutions, Protein Expression and Purification, Acad. Press, vol. 36, No. 2, 2004, pp. 244-248.

* cited by examiner

*Primary Examiner* — Daniel E Kolker
*Assistant Examiner* — James Rogers
(74) *Attorney, Agent, or Firm* — Michael P. Morris; Atabak R. Royaee

(57) ABSTRACT

The present invention relates to methods of depleting impurities, in particular host cell proteins (HCP) and DNA from cell culture supernatants by means of protein A chromatography using a novel washing buffer.

12 Claims, 10 Drawing Sheets

CHROMATOGRAPHIC METHOD FOR PURIFYING FC-CONTAINING PROTEINS

The invention relates to chromatographic methods for purifying proteins and agents for such methods.

Biomolecules such as proteins, polynucleotides, polysaccharides and the like are increasingly gaining commercial importance as medicaments, as diagnostic agents, as additives to foodstuffs, detergents and the like, as research reagents and for many other applications. The need for such biomolecules—e.g. in the case of proteins—can no longer generally be satisfied by isolating the molecules from natural sources but requires the use of biotechnological production methods.

The biotechnological preparation of proteins typically begins with the isolation of the DNA that codes for the desired protein, and the cloning thereof into a suitable expression vector. After transfection of the expression vector into suitable prokaryotic or eukaryotic expression cells and subsequent selection of transfected cells the latter are cultivated in fermenters and the desired protein is expressed. Then the cells or the culture supernatant is or are harvested and the protein contained therein is worked up and purified.

In the case of eukaryotic expression systems, i.e. when using mammalian cell cultures such as CHO or NS0 cells, for example, in the past 15 years there has been an increase by a factor of 100 in the concentration of the desired protein in the cell cultures or cell culture supernatants that can be achieved in the expression step. Over the same period the binding capacity of chromatographic materials that are used in the subsequent purification of the proteins has increased by a factor of 3. For this reason there is an urgent need for improved, optimised purification processes for biomolecules, particularly proteins, that can be carried out on a large industrial scale.

In the case of biopharmaceuticals, such as for example proteins used as medicaments, e.g. therapeutic antibodies, in addition to the yield of product the separation of impurities is also of crucial importance. A distinction may be drawn between process- and product-dependent impurities. The process-dependent impurities contain components of the host cells such as proteins (host cell proteins, HCP) and nucleic acids and originate from the cell culture (such as media constituents) or from the working up (such as for example salts or dissolved chromatography ligands). Product-dependent impurities are molecular variants of the product with different properties. These include abbreviated forms such as precursors and hydrolytic breakdown products, but also modified forms, produced for example by deamination, faulty glycosylations or wrongly linked disulphide bridges. The product-dependent variants also include polymers and aggregates. Other impurities are contaminants. By these are meant all other materials of a chemical, biochemical or microbiological nature which do not belong directly to the manufacturing process. Contaminants are for example viruses which may occur undesirably in cell cultures.

Impurities lead to safety concerns in the case of biopharmaceuticals. These are intensified if, as is very often the case in biopharmaceuticals, the therapeutic proteins are administered by injection or infusion directly into the bloodstream. Thus, host cell components may lead to allergic reactions or immunopathological effects. In addition, impurities may also lead to undesirable immunogenicity of the protein administered, i.e. they may trigger an undesirable immune response by the patient to the therapeutic agent, possibly to the point of life-threatening anaphylactic shock. Therefore, there is a need for suitable purification processes by means of which all undesirable substances can be depleted to an insignificant level.

On the other hand, economic aspects cannot be ignored in the case of biopharmaceuticals. Thus, the production and purification methods used must not jeopardise the economic viability of the biopharmaceutical product thus produced. In addition, the timescale within which a new purification process can be established plays an important role: Besides its influence on the costs, the process development must be in tune with the preclinical and clinical development of the drug. Thus, for example, some of the preclinical and all the clinical trials can only begin when sufficient quantities of the biopharmaceutical of sufficient purity are available.

The following standard process consisting of four basic steps may serve as a starting point for developing a purification process for an antibody which can be carried out on a large scale: In the first step the target protein is isolated, concentrated and stabilised ("capturing"). In the second step, viruses are eliminated, in the third step purification is carried out in which the majority of the impurities such as nucleic acids, other proteins and endotoxins are depleted. In the final step any remaining traces of contaminants are eliminated ("polishing").

In addition to filtration and precipitation steps, (column) chromatographic methods are of central importance. Thus, the capturing frequently includes a step of purification by affinity chromatography. Accordingly, there are numerous known column chromatographic methods and chromatography materials which can be used with them.

Affinity chromatography matrices, hereinafter also referred to as affinity matrices, are used as the stationary phase in the industrial purification of various substances. By means of immobilised ligands, it is possible to specifically enrich and purify substances that have a certain affinity for the particular ligand used. For the industrial purification of antibodies (immunoglobulins), particularly the purification of monoclonal antibodies, the use of immobilised protein A as the initial purification step has proved effective. Protein A is a protein with about 41 kDA of *Staphylococcus aureus*, that binds with high affinity ($10^{-8}$ M-$10^{-12}$ M of human IgG) to the $CH_2$/$CH_3$ domain of the Fc region of immunoglobulins. In protein A chromatography immunoglobulins or fusion proteins that have a protein-A-binding Fc region from the mobile phase bind specifically to the protein A ligand, which is covalently bound to a carrier (e.g. sepharose). Protein A from *Staphylococcus aureus* (wild-type protein A) and genetically modified recombinant protein A (rec. protein A) interacts, via non-covalent interactions, with the constant region (Fc fragment) of the antibodies. This specific interaction can be utilised to separate impurities efficiently from the antibody. By modifying the pH the interaction between antibody and protein A ligand can be deliberately stopped and the antibody can be released or eluted from the stationary phase.

The effectiveness of affinity chromatography can be increased if the stationary phase is washed after charging. Washing in this case means the application of a mobile phase that elutes impurities from the stationary phase, but not the target product. In the case of the affinity chromatography of antibodies by means of protein A matrices, washing buffers have been used which contain arginine, isopropanol, NaCl or a detergent (WO2008031020, WO2007109163, WO2007081906, WO2003066662, Millipore Tech Brief TB1026EN00), but not a combination of these components in a single washing buffer. A combination of two of these components, a salt and a detergent, i.e. a polymer such as e.g.

polyethylene glycol, polypropylene glycol and copolymers consisting thereof, was described in U.S. Pat. No. 6,870,034 B2.

SUMMARY OF THE INVENTION

Surprisingly it has been found that a certain combination of components in a single washing buffer in protein A chromatography leads to a higher degree of purity in a target protein that is to be purified than the separate use of the same components one after the other. The washing buffer according to the invention is, moreover, suitable for use in antibody purification on a standard basis and doing away with the optimising steps enables the process development to be shortened.

The invention relates to a method of depleting impurities from a composition which contains a protein that comprises the Fc domain of an immunoglobulin (target protein), by protein A chromatography, comprising the following steps:
a. applying a mobile phase which contains the target protein to a stationary phase which contains protein A, under conditions in which the target protein binds to the stationary phase;
b. applying a washing buffer with a pH of between 4 and 8 as mobile phase, containing as additives
   i. arginine in a concentration of 0.1-1 mol/l,
   ii. sodium chloride in a concentration of 0.2 to 2 mol/l,
   iii. an alcohol selected from among isopropanol, n-propanol and ethanol, in a concentration of 5-30% (w/v) and
   iv. polyvinylpyrrolidone and/or a detergent in a concentration of 0.05-2% (w/v);
c. using an elution buffer as mobile phase under conditions in which the target protein is eluted from the stationary phase.

In another aspect the washing buffer has a pH of from 4.5 to 8. In another aspect the washing buffer has a pH of from 5 to 8. In another aspect the washing buffer has a pH of from 6 to 8.

Preferably, the arginine concentration in the washing buffer is 0.4-0.6 mol/l, particularly 0.5 mol/l. The sodium chloride concentration in the washing buffer is preferably 0.9-1.1 mol/l, particularly 1 mol/l. The alcohol used in the washing buffer is preferably isopropanol in a concentration of 10-20% (v/v), particularly in a concentration of 15% (v/v).

Polyvinylpyrrolidone (PVP) is preferably used in a concentration of 0.1-2% (w/v) particularly 0.25% (w/v). In addition or alternatively, polyoxyethylene-sorbitan-monolaurate (Polysorbat 20, Polysorbat 80) may be used in a concentration of 0.05-2 (w/v).

In another aspect the present invention relates to a washing buffer for the affinity chromatography with a pH of pH 4 to pH 8, containing
   i. arginine in a concentration of 0.1-1 mol/l,
   ii. sodium chloride in a concentration of 0.2 to 2 mol/l,
   iii. an alcohol selected from among isopropanol, n-propanol, and ethanol, in a concentration of 5-30% (v/v), and
   iv. polyvinylpyrrolidone or a detergent in a concentration of 0.05-2% (w/v);

SPECIFIC DESCRIPTION OF THE INVENTION

Figure 1A:
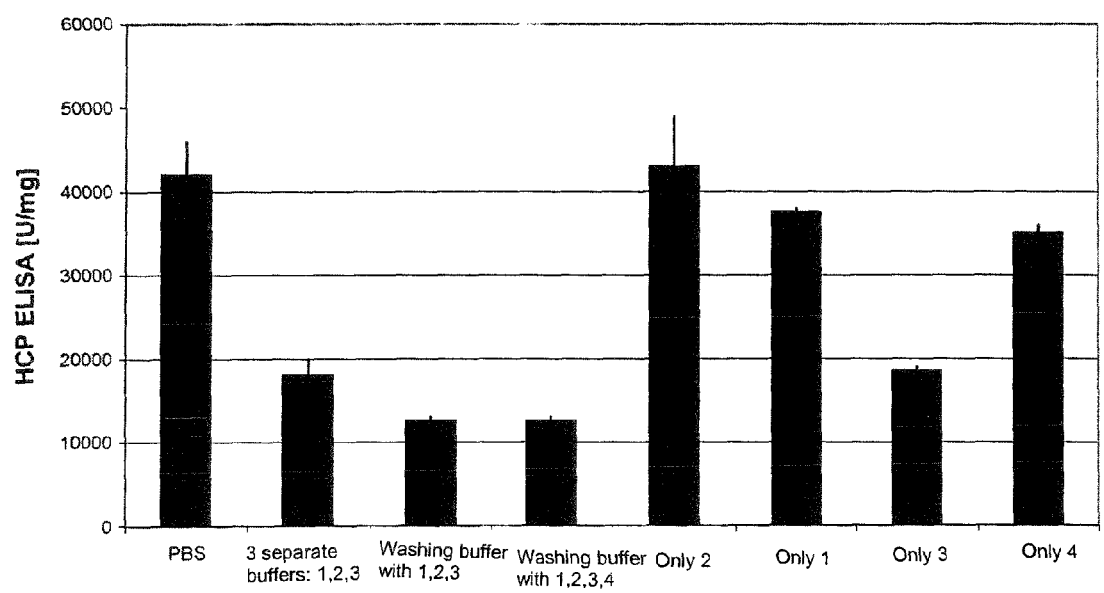
FIG. 1 shows the yields (1a), turbidities (1b), monomer contents (1c) and amount of HCP (1d) in the eluate from the affinity chromatography after washing with washing buffers in different combinations and of different compositions, taking the antibody BI-MAb 06a as an example. The numbers on the x axis relate to the additives to the washing buffer specified in the Example.
Figure 1B:
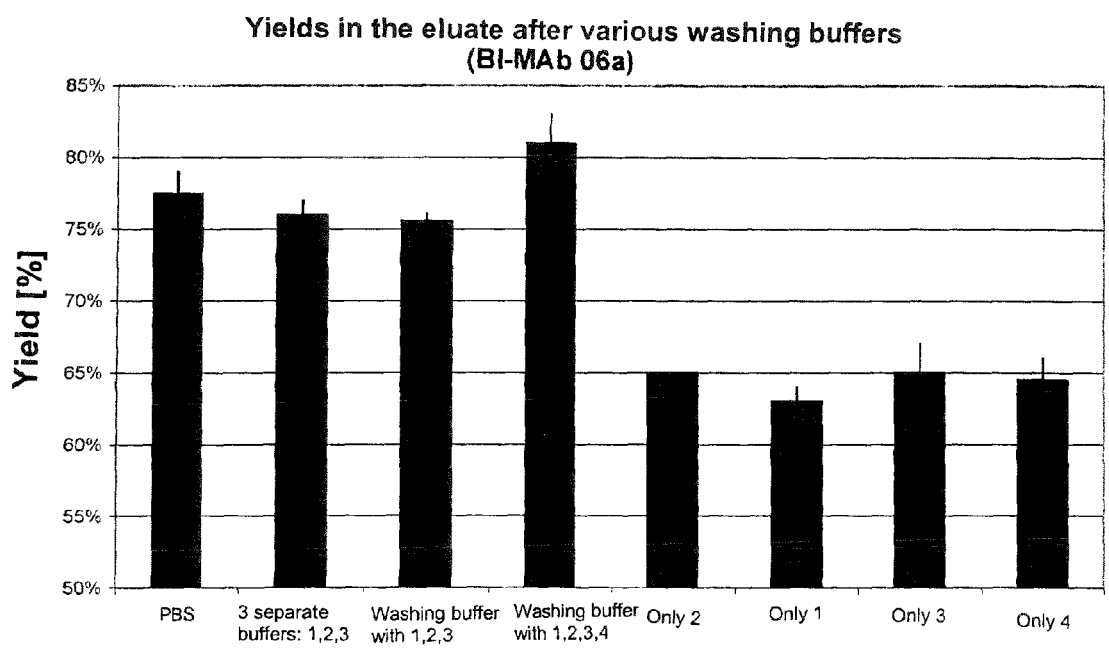
Figure 1C:
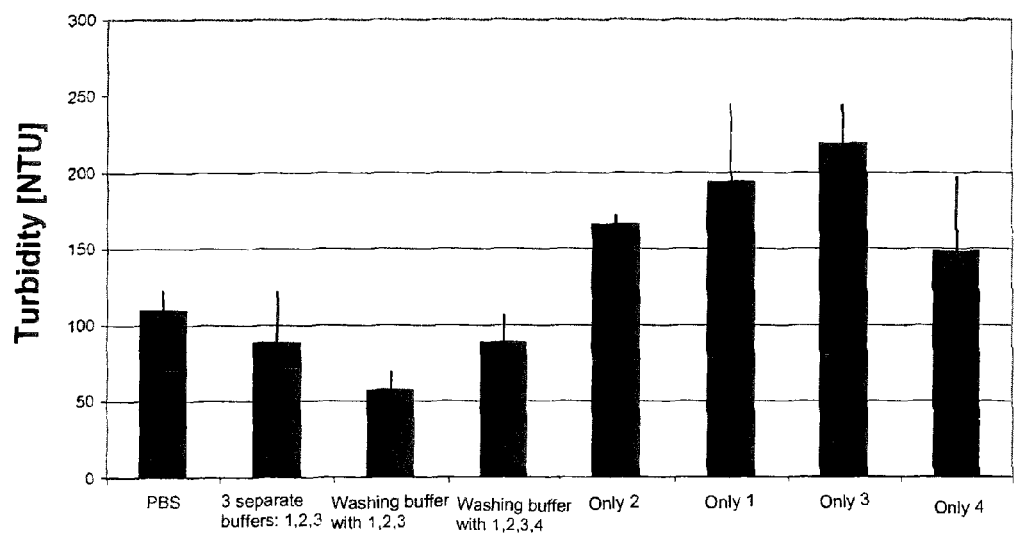
Figure 1D:
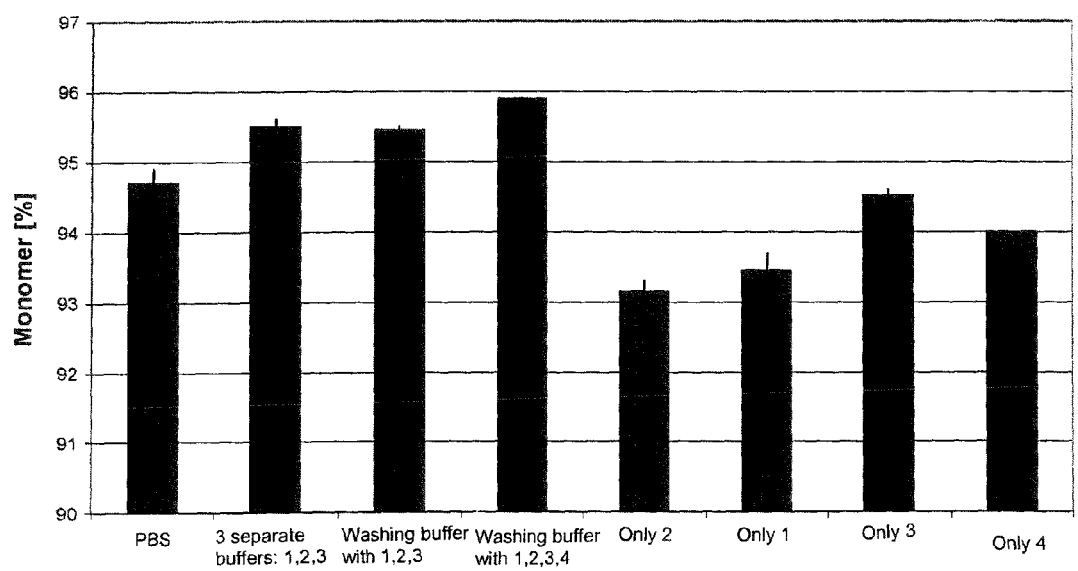
Figure 2A:
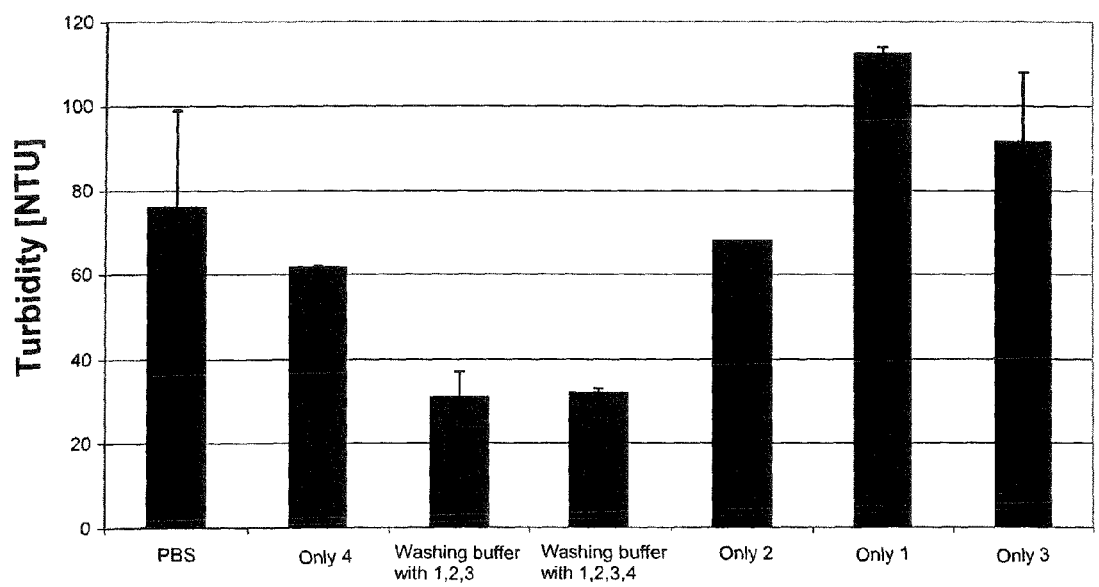
FIG. 2 shows the yields (2a), turbidities (2b), monomer contents (2c) and amount of HCP (2d) in the eluate from the affinity chromatography after washing with washing buffers in different combinations and of different compositions, taking the antibody BI-MAb 1003a as an example. The numbers on the x axis relate to the additives to the washing buffer specified in the Example.
Figure 2B:
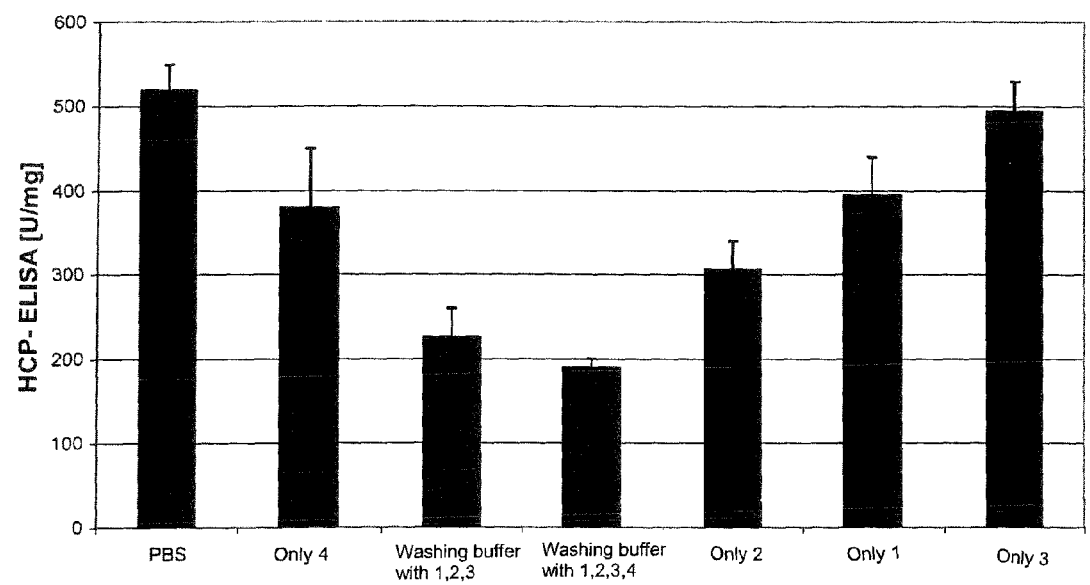
Figure 2C:
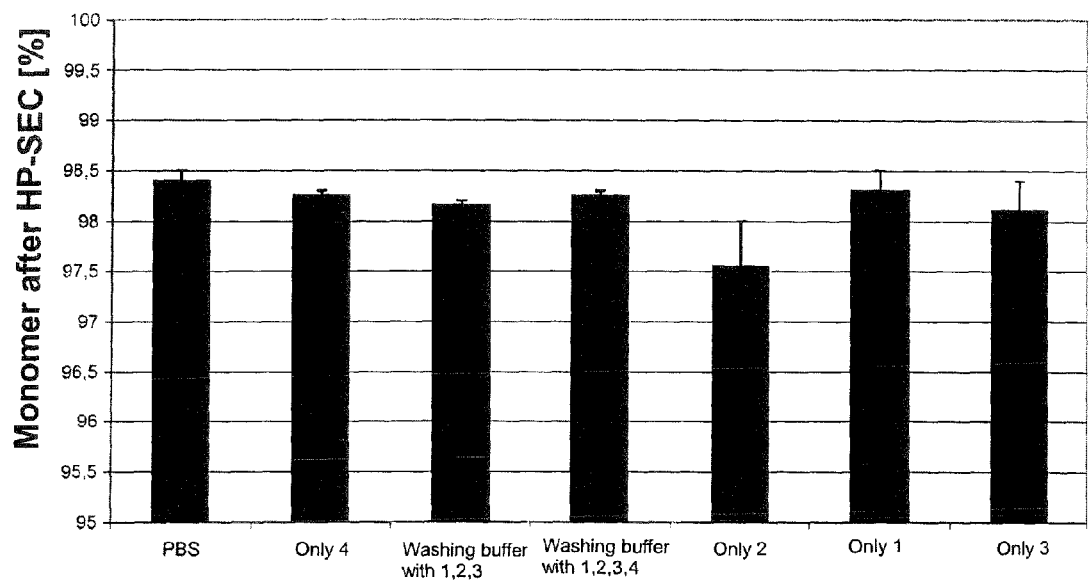
Figure 2D:
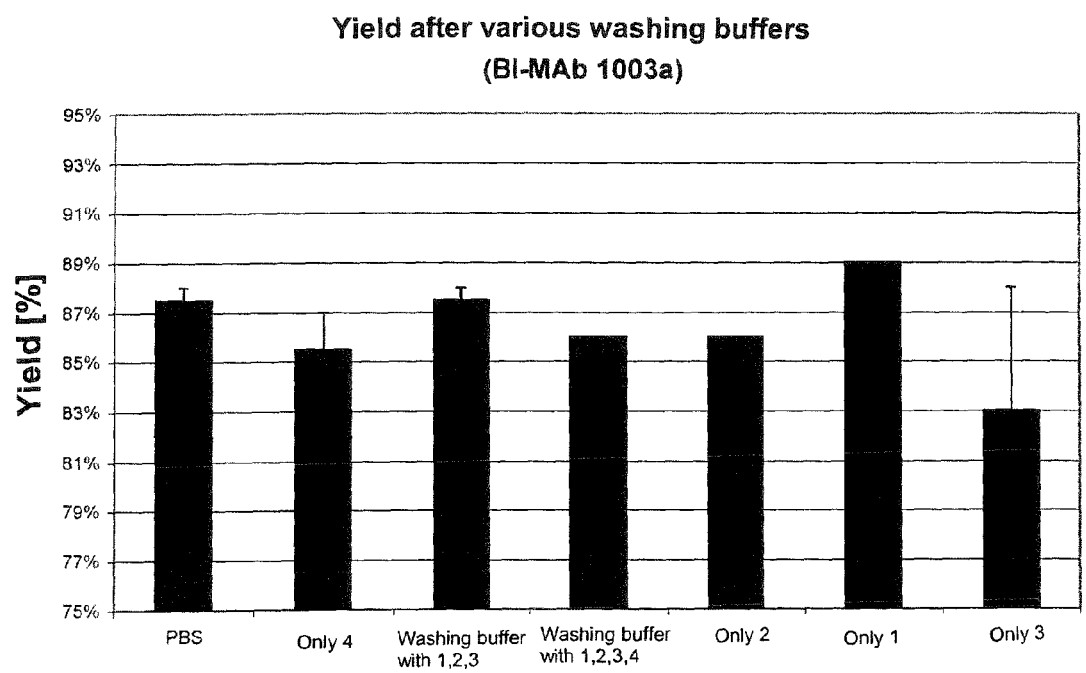
Figure 3:
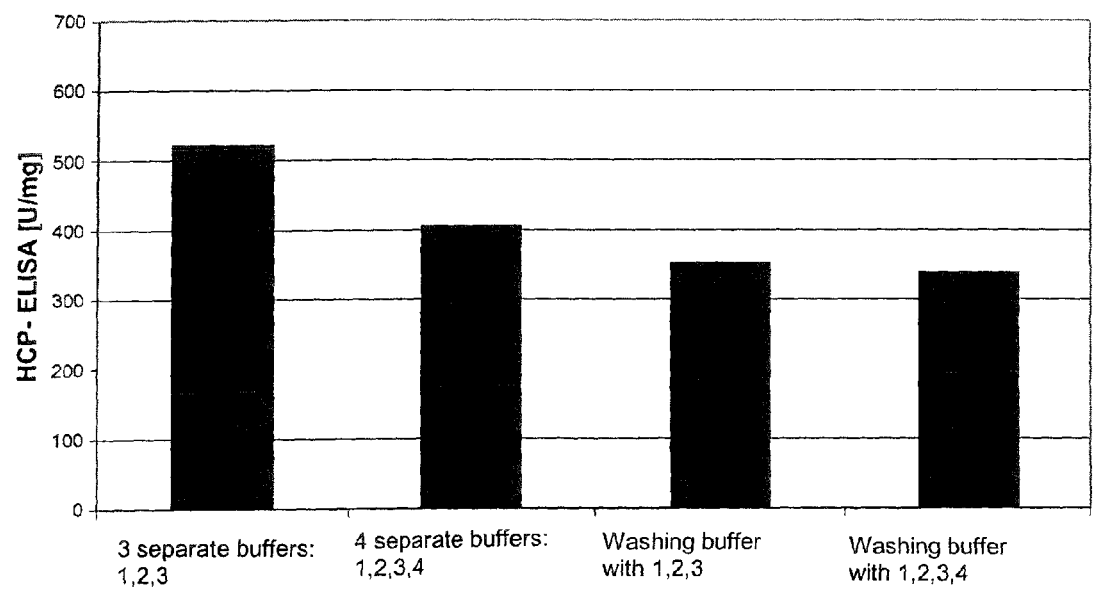
FIG. 3 compares the amount of HCP in the eluate from the affinity chromatography after washing with washing buffers in different combinations and of different compositions, taking the antibody BI-MAb 07c as an example. The numbers on the x axis relate to the additives to the washing buffer specified in the Example.
Figure 4:
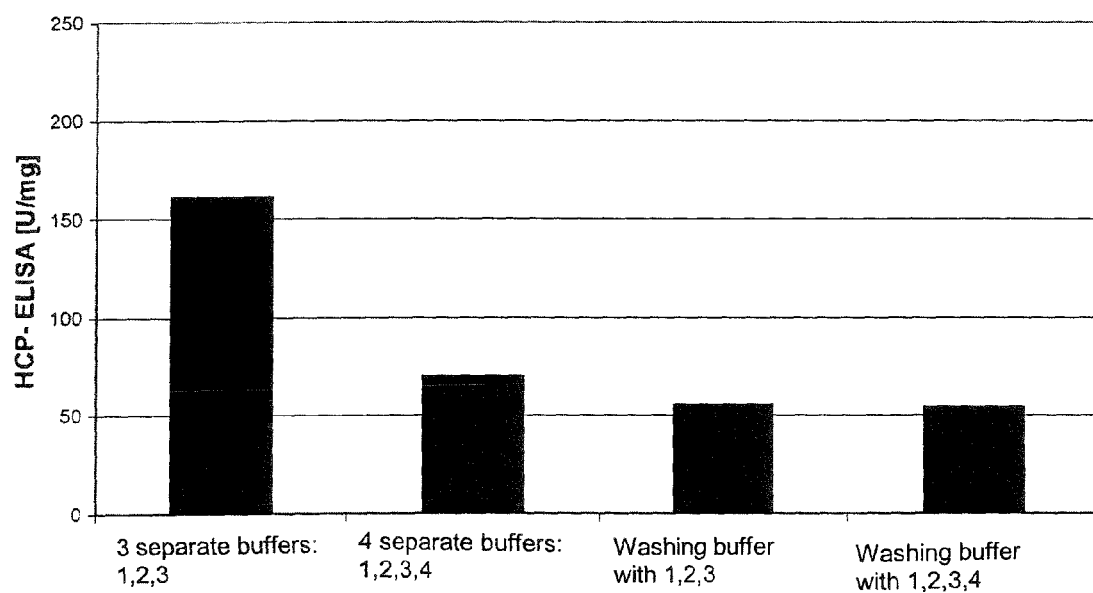
FIG. 4 compares the amount of HCP in the eluate from the affinity chromatography after washing with washing buffers in different combinations and of different compositions, taking the antibody BI-MAb 1001b as an example. The numbers on the x axis relate to the additives to the washing buffer specified in the Example.

The present invention relates to methods for depleting impurities, particularly host cell proteins (HCP) and DNA from protein compositions as obtained from cell cultures in which proteins are expressed recombinantly or endogenously. In particular the invention relates to methods for purifying or concentrating a protein (target protein) which can be reversibly immobilised on a stationary phase by means of a ligand and are thus amenable to affinity chromatography.

The target protein may be in particular an immunoglobulin or a protein which contains the Fc domain of an immunoglobulin and can bind to protein A. In a preferred embodiment these are immunoglobulins that consist of two heavy and two light immunoglobulin chains. Antibodies consist of two identical heavy chains (H) and two identical light chains (L) which are joined together by covalent disulphide bridges to form a Y-shaped structure. The light chains each consist of one variable and one constant domain, which are referred to as VL and CL. The heavy chains, on the other hand, each have one variable and three to four constant domains depending on the immunoglobulin. These are referred to analogously as VH and CH1, CH2, CH3. The variable domains of a light and a heavy chain form the antigen binding site. The domain CH2 contains a carbohydrate chain which forms a binding site for the complement system. The CH3 domain contains the Fc receptor binding site.

Protein A binds to the Fc domain of immunoglobulins by interactions with the heavy chain. The binding affinity is highest on human IgG1, IgG2 and IgG2a and on murine IgG2b. It binds with moderate affinity to human IgM, IgA, IgE and to murine IgG3 and IgG1.

However, it does not react either with human IgG3, IgD or with the following murine immunoglobulins: IgM, IgA and IgE.

Target proteins to which the method according to the invention may be applied are all those proteins that have an Fc domain, such as immunoglobulins. Immunoglobulins may be polyclonal or monoclonal antibodies which are expressed in hybridoma cells or recombinant host cells. Such antibodies may have been produced originally by immunising animals, particularly mammals, including transgenic animals, e.g. mice that express human immunoglobulins. Suitable target proteins also, however, include fusion proteins in which any desired protein and the Fc domain of an immunoglobulin have been fused.

Protein A matrices for the purposes of the invention are affinity chromatography matrices which contain immobilised protein as ligands. These include affinity matrices which contain wild-type protein A, for example from *Staphylococcus aureus* as ligand. A description of protein A can be found inter alia in Lofdahl, S. et al., 1983 (Lindmark, R., Thoren-Tolling, K., Sjoquist J (1983); Binding of immunoglobulins to protein A and immunoglobulin levels in mammalian sera: J Immunol Methods 1983 Aug. 12; 62(1):1-13.) and Lindmark et. al., 1983 (Lindmark, R., Thoren-Tolling, K., Sjoquist J (1983); Binding of immunoglobulins to protein A and immunoglobulin levels in mammalian sera: J Immunol Methods 1983 Aug. 12; 62(1):1-13.). In addition, the invention also relates to matrices with recombinantly produced protein A as ligand. Recombinant protein A is described by way of example by Duggleby C. J. and Jones, S. A., 1983 (Duggleby, C. J. and Jones, S. A. (1983), Cloning and expression of *Staphylococcus aureus* protein A gene in Escherichia coli. Nucl. Acid. Res. 1983 May 25; 11(10):3065-76.) or Li, R. et al., 1998 (Li, R. Dowd, V., Stewart, D. J., Burton, S. J. Lowe, C. R., Design, Synthesis and application of a protein A mimetic. Nat. Biotechnol. 1998 February; 16(2):190-5.) and is known in the art.

The protein A may be coupled to various carrier materials such as for example agaroses, polysaccharides, dextranes, silica gels and glass beads. A non-definitive list of suitable carrier materials can be found in Harlow, E. and Lane, D. 1999. One carrier material that is frequently used is formed by agarose-based materials such as for example the "sepharoses" made by Amersham Pharmacia Biotech, Uppsala, Sweden, which are known to the skilled man. Particular examples of protein A sepharoses can be found in the Manual produced by this company on the subject of "Affinity Chromatography" dating from 2001. Furthermore, other protein A chromatography matrices are known to the skilled man such as for example MabSelect (Amersham Pharmacia Biotech, Uppsala, Sweden), STREAMLINE™ rProtein A, (Amersham Pharmacia Biotech, Uppsala, Sweden), Poros A (Millipore, Durham, England). The method according to the invention includes a treatment of the corresponding matrices, the list of matrices being provided by way of example and without claiming to be exhaustive.

The coupling of the ligand is generally carried out by means of free amino, carboxyl or sulphur groups by cyanogen bromide activation, NHS activation or thiol coupling to the carrier matrix. Cf. on this subject, for example, the manual "Affinity Chromatography", Amersham Pharmacia Biotech, Uppsala, Sweden, 2001.

In a particularly preferred embodiment polyvinylpyrrolidone (PVP, also known as Polyvidone or Povidone, CAS: 9003-39-8) is used in the washing buffers according to the invention. Polyvinylpyrrolidone is a water-soluble polymer consisting of N-vinylpyrrolidone monomer units. However, it may also be dissolved in other polar solvents. PVP is a hygroscopic amorphous powder that is white to pale yellow in colour. The standard commercial polymers have a molar mass in the range from about 2500 to 2,500,000 Dalton.

In the washing buffers of the present invention detergents may be used in addition to or instead of PVP. Detergents are surfactant and amphiphilic molecules which can form micelles, i.e. aggregates of detergent molecules, wherein the hydrophilic head faces outwards towards the aqueous solvent.

Detergents for the purposes of the invention are both non-ionic and ionic substances. However, non-ionic detergents are preferred, such as e.g. polyglycolether (type NP-40, Tergitol NP40, CAS: 127087-87-0), a PEG-alkylether polyoxyethylene(23)laurylether (CAS: 9002-92-0), PEG-sorbitan fatty acid ester such as polyoxyethylene(20)sorbitan-monolaurate (Polysorbat 20, CAS: 9005-64-5) or polyoxyethylene (20) sorbitan-monooleate (Polysorbat 80, CAS: 9005-65-6), alkylphenyl-PEG-ethers such as t-octylphenoxypolyethoxyethanol (Triton-X-100, CAS: 9002-93-1), or PEO-PPO block copolymer (poloxamer derivatives), such as polyoxyethylene-polyoxypropylene block copolymer (Pluronic F 68, Lutrol F 68, Poloxamer 188, CAS: 9003-11-6 or Poloxamer 407, Pluronic F 127, Lutrol F 127, CAS: 9003-11-6).

The pH values of the washing and eluting buffers are dependent on the system as a whole and are therefore generally individually determined and optimised for each system.

In one aspect the washing buffer has a pH of 4 to 8. The skilled man is familiar with the fact that the pH at which a protein is eluted from a column is dependent on a number of factors. These might include, inter alia, the buffer systems using during binding, washing and elution, the presence of impurities, the geometry of the matrix particles, the nature of the coupling of the affinity ligand to the chromatography matrix. In particular the specific properties of the protein have a decisive influence.

In some cases there may be combinations with which partial or total elution of the protein from the affinity ligand may occur even above a pH of 4. In such a case, and if a loss of protein is not acceptable, the washing buffer must have a higher pH. The skilled man is aware that in such cases he must adjust the pH of the washing buffer accordingly. In most cases, however, the binding between the protein and the protein A affinity ligand will only be undone below pH 4.

In another aspect the washing buffer has a pH of 4.5 to 8. In another aspect the washing buffer has a pH of from 5 to 8. In another aspect the washing buffer has a pH of from 6 to 8.

In a typical embodiment the invention may be carried out as follows, for example:

Protein A chromatography is generally the first purification step. The cell-free cell culture supernatant can be added directly to the column, or first of all a concentration may be produced through an ultrafiltration membrane, a so-called UF/DF system.

The protein A column is first equilibrated with phosphate buffer (PBS), which roughly corresponds in its physico-chemical properties to the charging pool. The charging pool consists of the supernatant from the cell culture which contains the product to be purified and also additional media constituents that are necessary for growing the mammalian cells in question, such as for example CHO or NS0 cells. This cell-free supernatant of the cell culture or a concentrate thereof is charged onto the protein A column. The target protein then binds to the protein A binding site on the column. Then the column is flushed with equilibrating buffer until the non-bound media constituents and cell products have been eluted. The washing buffer described can be added after the equilibration buffer or directly after charging. The quantity of washing buffer is dependent on the scale and is therefore given in relation to the size of the chromatography column.

Usually the volume of washing buffers is roughly 2 to 5 times the volume of the chromatography column (2-5 bed volumes, BV). After the addition of the washing buffer the column can be treated again with the equilibration buffer or another buffer so that no constituents of the washing buffer are eluted with the product. The buffer used here must have a pH which is lower than that of the washing buffer but higher than that of the eluting buffer and resembles the elution buffer in buffer salt and composition. A buffer with a pH of less than 4 is used for the elution and may contain as its main ingredient the acetate or citrate salt, for example. Eluting buffers may contain an acetate in concentrations of between 10 mM and 200 mM, preferably between 20 mM and 100 mM, most preferably 50 mM and 100 mM, or may contain citrate in concentrations of between 10 and 200 mM, preferably between 20 and 100 mM. Both buffers should be in the above-mentioned pH range of less than 4, preferably between 3 and 4, particularly preferably between 3.4 and 3.6. Moreover, additives such as arginine or PVP may also be present. Furthermore, a glycine buffer may be used in concentrations of between 10 and 200 mM, preferably between 25 and 100 mM, with a pH of between 2 and 3.5, or other buffers that are suitable for reducing the binding between the Fc domain of the antibody and the protein A. The eluate can then be worked up further in the following process, for example incubation at a lower pH or neutralisation.

EXAMPLES

Experiments were carried out with various proteins obtained from different cell lines (CHO and NS0), which were fermented in different media, and the Fc parts of which belonged to different IgG subtypes (IgG1, IgG2, IgG4).

Test series were carried out in which, starting from the standard, only the washing buffer or buffers were changed. Either the equilibration buffer was introduced without any additive, a washing buffer was used with only one additive, a number of different buffers were added sequentially, each with one additive, or a washing buffer with a combination of a number of additives was used.

The protein solution applied was always the same for the respective protein.

Each test measured the amount of impurities in the eluate. By comparisons between the experiments, the washing buffer after which the eluate had the smallest possible amounts of the respective impurities was identified. In some experiments, yields, turbidities and monomer contents were also measured.

Chromatography

The chromatography experiments were carried out on an automated AKTA-FPLC Model 900 system (GE Healthcare). Four different products were used for the experiments. Of the products, either the cell-free culture supernatant or concentrated culture supernatant was used as starting material, the preparation being concentrated tenfold with a 50 kD Omega membrane (Pall) and then diafiltered three times with PBS.

The columns used had a volume of 1 ml to 8 ml and contained one of the chromatography gels MabSelect or MabSelect Xtra (GE Healthcare).

Buffer

In all the experiments a phosphate buffer (PBS) with 10 mM phosphate, 5 mM potassium chloride and 140 mM sodium chloride at pH 7.4 was used as the equilibration buffer.

All the washing buffers were based on a PBS buffer (pH 7.4) containing
8 mmol/L sodium monohydrogen phosphate,
1.5 mmol/L potassium hydrogen phosphate,
2.7 mM potassium chloride and
140 mM sodium chloride.

As additives, the following were used, individually or in various combinations (as specified in the Figures):
(1) 860 mmol/L sodium chloride (total content 1 mol/L sodium chloride)
(2) 0.25% (w/V) polyvinylpyrrolidone (PVP)
(3) 15% (V/V) isopropanol
(4) 0.5 mol/L L-arginine For the elution, depending on the product, a different buffer was used, with different acetate concentrations and pH. The following concentrations were used:
BI-Mab 06a: 100 mM acetate pH 3.4

BI-Mab 1003a: 50 mM acetate pH 3.4
BI-Mab 1001b: 50 mM acetate pH 3.4
BI-Mab 07c: 50 mM acetate pH 3.6

Analyses

The eluates of the experiments were compared for their content of impurities and the yields were determined.

To determine the amount of cell constituents a generic sandwich ELISA was used, and the host cell proteins were determined as empirical parameters. For the assay polyclonal detection antibodies were used.

The monomer content was determined using the Agilent Series HPLC 1200 (waters) system and depending on the protein a TSK 3000SW or a TSK 3000SWXL column (TosoH). The isocratic method operates with a flow rate of 1 ml/min with a Tris buffer at pH 7.0.

The DNA is determined by the threshold method (Kung, V. T. et al., Picogram Quantitation of Total DNA Using DNA-Binding Proteins in a Silicon Sensor-Based System, Anal. Biochem. 1990, 187, 220-227).

A Phast system (GE Healthcare) is used to carry out a SDS-PAGE. The samples are separated using a Phast SDS gel (4%-15%, GE). Staining is done using Heukeshoven silver staining (Heukeshoven, Dernick 1988, Electrophoresis 9 (1), pages 28-32).

In order to determine the amount of antibody in the charge and in the eluate, a PA 2-1001-00 protein A column (Applied Biosystems) and an Agilent Series 1200 HPLC system (waters) was used. The binding and elution were carried out over a gradient from pH 7.4 to pH 2.8 in the PBS buffer system, evaluation was done using an external calibrating line of the antibody in question.

The turbidity measurement was carried out in the 2100AN Turbidimeter (Hach) after calibration with the manufacturer's turbidity standards.

Results

Experiments with BI-MAb 06a, an Antibody of Sub-Class IgG1

The results show a significant effect of the washing on the yield, monomer, turbidity and host cell proteins (HCP).

In the quality criteria of yield, monomer content and HCP depletion, the eluate shows the best value after washing with the buffer that contains all four additives. Moreover, the combination of the additives leads to a substantial reduction in turbidity, both with the combination of the three ingredients 0.86 mol/L sodium chloride, 0.25% (w/V) PVP and 15% (V/V) isopropanol, and with the combination of all four additives 0.86 mol/L sodium chloride, 0.25% (w/V) PVP, 15% (V/V) isopropanol and 0.5 mol/L arginine.

Experiments with BI-MAb 1003a, an Antibody of Subclass IgG1

The best HCP depletion is achieved with the washing buffer that contains all four additional components. Similarly good values are obtained with the washing buffer with the combination of sodium chloride, PVP and isopropanol. More HCP is obtained in the eluate by washing with buffers that contain the four components individually.

With the turbidities too, the combination of the washing substances in a buffer gives a better result.

Experiments with BI-MAb 07c, an Antibody of Subclass IgG4

The eluates from the tests on the individual washing buffers have higher levels of HCP than the eluates from the tests with combined washing buffers.

Experiments with BI-MAb 1001 b, an Antibody of Subclass IgG2

The eluates from the tests on the individual washing buffers have higher levels of HCP than the eluates from the tests with combined washing buffers.

The four experiments show that the combination of the four additives sodium chloride, PVP, isopropanol and arginine in a single washing buffer has an advantage over the use of washing buffers with individual additives in relation to the content of host cell proteins (HCP) in the eluate.

The use of the washing buffer described also shows that turbidities in the eluate are significantly reduced. The amount of monomer and the yield are also improved (BI-MAb 06a), or at least remain the same (BI-MAb 1003a).

The washing buffer described is therefore suitable for significantly improving the production process for proteins. The introduction of the combination of washing buffers depletes the impurities that would otherwise have to be removed by an additional purification step.

The invention claimed is:

1. A method of depleting impurities from a composition that contains a protein which comprises the Fc domain of an immunoglobulin (target protein), by protein-A chromatography, comprising the steps of:
   a. applying a mobile phase which contains the target protein to a stationary phase which contains protein A, under conditions in which the target protein binds to the stationary phase;
   b. applying a washing buffer with a pH of between 4 and 8 as mobile phase, containing
      i. arginine in a concentration of 0.1-1 mol/l,
      ii. sodium chloride in a concentration of 0.2 to 2 mol/l,
      iii. an alcohol selected from among isopropanol, n-propanol and ethanol, in a concentration of 5-30% (w/v) and
      iv. polyvinylpyrrolidone in a concentration of 0.05-2% (w/v);
   c. using an elution buffer as mobile phase under conditions in which the target protein is eluted from the stationary phase.

2. The method according to claim 1, wherein the arginine concentration in the washing buffer is 0.4-0.6 mol/l.

3. The method according to claim 1, wherein the sodium chloride concentration in the washing buffer is 0.9-1.1 mol/l.

4. The method according to claim 1, wherein the alcohol in the washing buffer is isopropanol in a concentration of 10-20% (w/v).

5. The method according to claim 1, wherein polyvinylpyrrolidone (PVP) is in a concentration of 0.1-2% (w/v).

6. The method according to claim 1, wherein the impurities are host cell proteins (HCP).

7. A method of depleting impurities from a composition that contains a protein which comprises the Fc domain of an immunoglobulin (target protein), by protein-A chromatography, comprising the steps of:
   a. applying a mobile phase which contains the target protein to a stationary phase which contains protein A, under conditions in which the target protein binds to the stationary phase;
   b. applying a washing buffer with a pH of between 5 and 8 as mobile phase, containing
      i. arginine in a concentration of 0.1—1 mol/l,
      ii. sodium chloride in a concentration of 0.2 to 2 mol/l,
      iii. an alcohol selected from among isopropanol, n-propanol and ethanol, in a concentration of 5—30% (w/v) and
      iv. polyvinylpyrrolidone in a concentration of 0.05—2% (w/v);
   c. using an elution buffer as mobile phase under conditions in which the target protein is eluted from the stationary phase.

8. The method according to claim 7, wherein the arginine concentration in the washing buffer is 0.4—0.6 mol/l.

9. The method according to claim 7, wherein the sodium chloride concentration in the washing buffer is 0.9—1.1 mol/l.

10. The method according to claim 7, wherein the alcohol in the washing buffer is isopropanol in a concentration of 10—20% (w/v).

11. The method according to claim 7, wherein polyvinylpyrrolidone (PVP) is in a concentration of 0.1—2% (w/v).

12. The method according to claim 7, wherein the impurities are host cell proteins (HCP).

* * * * *